United States Patent [19]

Wang et al.

[11] 4,138,409

[45] Feb. 6, 1979

[54] EPOXYSULTONE

[75] Inventors: Patricia C. Wang; Robert E. Wingard, Jr., both of Palo Alto, Calif.

[73] Assignee: Dynapol, Palo Alto, Calif.

[21] Appl. No.: 929,622

[22] Filed: Jul. 31, 1978

Related U.S. Application Data

[63] Continuation-in-part of Ser. No. 863,117, Dec. 22, 1977, abandoned.

[51] Int. Cl.² ............................................. C07D 327/04
[52] U.S. Cl. ................................. 260/327 S; 426/548
[58] Field of Search ...................................... 260/327 S

[56]   References Cited
       U.S. PATENT DOCUMENTS 3,980,669   9/1976   Sundby et al. ................... 260/327 S

OTHER PUBLICATIONS

Gevaert Photo–Producten N.V., Chem. Abstracts, vol. 51, col. 17545, (1957), (Abstract of Belgian Patent 535,688).
Breslow et al., Multi-Sulfur and Sulfur and Oxygen 5-and 6-Membered Heterocycles, Part One, pp. 76 to 95, Interscience Publishers, New York, (1966).
Mustafa, Chemical Reviews, vol. 54, pp. 195 to 198, (1954).

*Primary Examiner*—John D. Randolph
*Attorney, Agent, or Firm*—William H. Benz

[57]         ABSTRACT

A new compound, denominated epoxysultone, having the structure

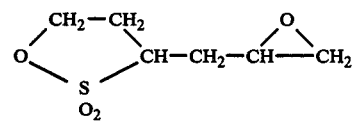

is disclosed. The compound is an electrophilic addition agent of broad application which finds especial use in the preparation of new sweetener compounds. An intermediate to epoxysultone is also disclosed.

2 Claims, No Drawings

EPOXYSULTONE

CROSS-REFERENCE TO RELATED APPLICATION

This application is a continuation-in-part of our earlier copending application, Ser. No. 863,117, filed Dec. 22, 1977, now abandoned, hereby expressly incorporated by reference in its entirety and relied upon.

BACKGROUND OF THE INVENTION

The present invention provides a new electrophilic addition agent. This material is attractive as it is bifunctional — having, in a relatively very small molecule, an active epoxide group and an active sultone group. The sultone group can function chemically in a manner analogous to propane sultone, the epoxide in a manner analogous to ethylene oxide.

STATEMENT OF THE INVENTION

The present invention is epoxysultone, that is, a compound as shown in General Formula I.

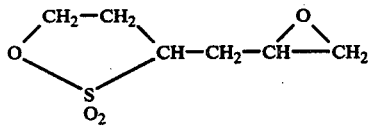

Another aspect of this invention is 1-oxa-2-thia-3-(2-propenyl) cyclopentane 2,2-dioxide, a compound shown in General Formula II.

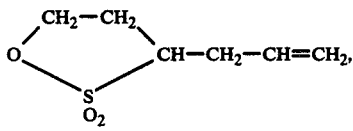

which is an intermediate in the synthesis of epoxysultone.

DETAILED DESCRIPTION OF THE INVENTION

The compound of this invention and its intermediate, having been fully set forth above, this part of the specification will show the preparation of the epoxysultone compound and demonstrate its use.

PREPARATION

Propane sultone, 3.84 g, was dissolved in 200 ml of freshly distilled THF in a 500 ml round bottomed flask. The flask was capped, deaerated and cooled with a dry ice-acetone bath for one-half hour. Under argon, n-butyllithium in hexane (1.10 equiv.) was added in five minutes. After stirring for five minutes at −78° C., allyl bromide (3.4 ml, 1.25 equiv.) was added in five minutes. The clear, colorless solution was stirred under argon at −78° C. for two hours. The reaction mixture was poured into a separatory funnel containing 500 ml of ethyl acetate and 250 ml of water, and shaken. Two phases formed. The aqueous phase was discarded. The organic phase was washed with brine, dried over MgSO₄ and evaporated to remove solvent. The product was 4.81 g (94% yield) of a clear, viscous oil which was shown to be 1-oxa-2-thia-3-(2-propenyl)cyclopentane 2,2-dioxide

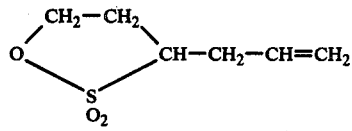

by H NMR spectrum in CDCl₃. This intermediate is believed to be a new compound.

This material (3.70 g) was epoxidized by dissolving in 100 ml of dry methylene chloride, adding m-chloroperbenzoic acid (85% pure, 6.96 g, 1.5 equivalents), and heating at reflux for two days. The reaction was cooled, and filtered to remove some white solid which had formed. The liquid was washed with 20% NaHSO₃ (100 ml portions, five times), saturated NaHCO₃ (250 ml portions, four times), brine (250 ml portions, two times) and dried over MgSO₄ and evaporated to dryness. A crude white material (3.18 g) is recovered, dissolved in 45 ml of chloroform and subjected to column chromatography on a silica gel column with chloroform as eluent. A fraction was taken and evaporated to yield 1.7 g (42% yield). The clear oil which resulted was shown by TLC and elemental analysis to be pure, and by NMR to be the desired epoxysultone of General Formula I.

Use of the Epoxysultone

The epoxysultone (0.35 g) prepared above was dissolved in 4 ml of dry DMF. Hesperetin (0.66 g, 1.1 equivalents — Sigma Chemical) was added. The mixture was stirred for ten minutes under argon at room temperature. Potassium carbonate (0.30 g, 1.1 equivalents) was added and the mixture was stirred at room temperature under argon for 42 hours. The mixture was filtered to remove solid and the filtrate evaporated to give a thick oil which by high-pressure liquid chromatography (HPLC) was seen to contain the desired product, hesperetin epoxysulfonate, and a small amount of unreacted hesperetin:

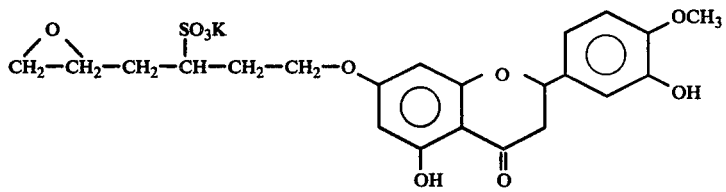

The epoxysulfonate was placed in a 250 ml flask. Glacial acetic acid (17.5 ml) and 0.05 M sulfuric acid (40 ml) were added and the mixture maintained at 60° C. for 46 hours, cooled, and evaporated on a rotary evaporator. The residue was dissolved in 250 ml of water, washed with five 250-ml portions of ethyl acetate and evaporated to about 40 ml. By HPLC, quantitative ring opening of the epoxide group had been achieved.

The product of the ring opening was then placed under argon in a Parr hydrogenation apparatus. The apparatus was charged with 36 psi of hydrogen, a 5% palladium on charcoal catalyst (0.3 g) and dilute aqueous KOH (4.02 M, 5.0 ml). After 17 hours at room temperature, the reaction product was removed, filtered through Celite, acidified with HCl, evaporated to dryness, redissolved in water, and separated by preparative HPLC into its components. One component, which isolated 99% pure, was studied by NMR, and elemental analysis and confirmed to be the dihydroxyhexoxy dihydrochalcone:

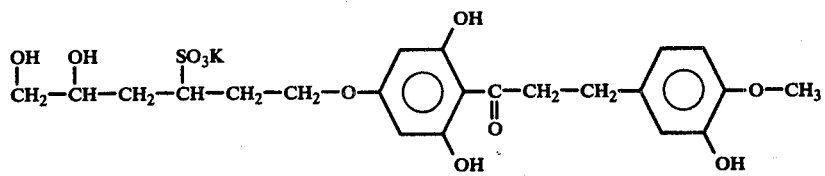

Such dihydroxyhexoxy dihydrochalcone is sweet; same finds use as a non-sucrose sweetener for edibles such as foods, medicaments, beverages and other comestibles, and as is more fully described in copending application to Wang et al, Ser. No. 863,116, filed Dec. 22, 1977, assigned to the assignee hereof, and also hereby expressly incorporated by reference in its entirety and relied upon.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. The compound

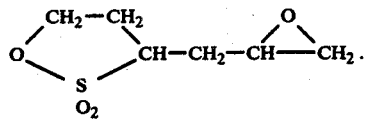

2. The compound

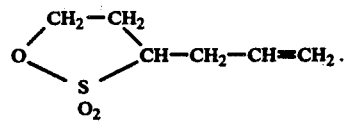

* * * * *